United States Patent [19]

Godfrey et al.

[11] 3,952,096

[45] Apr. 20, 1976

[54] MIXTURE OF CALCIUM CARBONATE AND CALCIUM-α-p-CHLOROPHENOXYISOBUTYRATE AS AN ANTIHYPERLIPEMIC AGENT

[75] Inventors: John Carl Godfrey, Syracuse; John Edwin MacNintch, Liverpool; Joseph Rubinfeld, Northport, all of N.Y.

[73] Assignee: Bristol-Myers Company, New York, N.Y.

[22] Filed: June 15, 1973

[21] Appl. No.: 370,506

[52] U.S. Cl. .......................... 424/156; 260/521 H; 424/317; 424/357; 424/360; 424/362; 424/365
[51] Int. Cl.² .................. A61K 31/19; A61K 33/00
[58] Field of Search ........................... 424/317, 156

[56] References Cited
UNITED STATES PATENTS 3,262,850  7/1966  Jones et al. .................. 424/317 X

OTHER PUBLICATIONS

Chemical Abstracts I (Maibach), Vol. 66, 103983q (1967).

Chemical Abstracts II, Vol. 73, 13070e, (1970).

Primary Examiner—Sam Rosen
Assistant Examiner—Vera C. Clarke
Attorney, Agent, or Firm—David M. Morse; Herbert W. Taylor, Jr.

[57] ABSTRACT

Calcium α-p-chlorophenoxyisobutyrate, particularly as its novel monohydrate, when combined with about one to two parts by weight of calcium carbonate in oral dosage form for use in mammals, and especially man, provides a safe and effective composition for reducing elevated blood levels of cholesterol, triglycerides and/or low density lipoproteins and/or increasing fibrinolytic activity and/or decreasing platelet aggregation. A preferred embodiment is a capsule containing 500 mgm. calcium carbonate and 250 or 500 mgm. crystalline calcium α-p-chlorophenoxyisobutyrate monohydrate having the empirical formula $C_{10}H_{10}ClO_3Ca_{1/2} \cdot H_2O$.

10 Claims, No Drawings

MIXTURE OF CALCIUM CARBONATE AND CALCIUM-α-p-CHLOROPHENOXYISOBUTYRATE AS AN ANTIHYPERLIPEMIC AGENT

BACKGROUND OF THE INVENTION

1. Field of the Invention

The chemicals of the present combination are used in therapy in man, as of arteriosclerosis, to reduce blood levels of cholesterol, triglycerides and lipo proteins, to increase fibrinolytic activity and to decrease platelet aggregation.

2. Description of the Prior Art

The method of reducing the cholesterol content of blood, particularly in man, which comprises the oral administration of p-chlorophenoxyisobutyric acid (CPIB) and the lower alkyl esters and alkaline earth metal salts thereof including its calcium salt is disclosed in U.K. Patent Specification No. 860,303, Canada Pat. No. 707,737 and U.S. Pat. No. 3,262,850. It is stated therein that:

"The compositions described above may in addition contain dietary supplements, for example, vitamins, salts of glycerophosphoric acid, choline and inositol, the combination of which is known to be effective in reducing serum cholesterol levels, and amino acids, for example, methionine which has a lipotropic action similar to choline."

The ethyl ester has found extensive use in medicine under the generic name of clofibrate (e.g. as "ATROMID-S") and in combination with androsterone (as "ATROMID"). Various amine salts have also been used, e.g. as by Spreafico, Arzneim.-Forsch. 23(2), 236–239 (1973) and so have amides, e.g. U.S. Pat. No. 3,629,453. The aluminum salt is disclosed in Switzerland Pat. Nos. 423,748 and 452,459. Combinations with androstone derivatives are disclosed in U.K. Patent Specification No. 898,596 and with heparinoid in Belgium Pat. No. 669,411.

The utility of oral clofibrate therapy in the management of Fredrickson Type III and Type IV hyperlipemias in humans is well documented; see Krasno, L. R., and G. J. Kidera: Clofibrate in coronary heart disease. Effect on morbidity and mortality, JAMA 219(7): 845–851 (1972).

Unsigned: Trial of clofibrate in the treatment of ischaemic heart disease. Five-year study by a group of physicians of the Newcastle upon Tyne region, Brit. Med. J. 4: 767–775 (1971).

Unsigned: Ischaemic heart disease? A secondary prevention trial using clofibrate, Report by a research committee committe of the Scottish Society of Physicians, Brit. Med. J. 4: 775–784 (1971). It is firmly established that calcium in the form of calcium carbonate administered orally produces hypochlesteremic effects in human Type II and Type IV hypercholesteremics; see Bierenbaum, M. L., A. I. Fleischman and R. I. Raichelson: Long term human studies on the lipid effects of oral calcium, LIPIDS 7(3): 202–206 (1972). of the same magnitude as does clofibrate in Types III and IV. To the extent that mechanisms of hypocholesteremic action are known, it appears that each of these agents acts differently from the other, and that the degree of hypocholesteremia induced by each seems to be limited to about 25% (although the degree of hypocholesteremia is highly variable among human subjects). Combinations of hypocholesteremic agents have been strongly suggested as being of potential value in the management and prevention of cardiovascular disease; see Parson, Jr., W. B.: Treatment of hyperlipidemia: The rationale for combinations of lipid-lowering drugs, Clin. Med.: 15–20, November, 1971.

The desirability of reducing the adhesiveness and aggregation of blood platelets as a method for preventing the formation of thrombi and emoboli in mammals is well-known and has been discussed, for example in U.S. Pat. No. 3,646,195.

Considerable effort has been directed in recent years to obtain substances which are useful in the treatment of hyperlipidemia, a condition associated with elevated cholesterol, phospholipid and/or triglyceride blood levels. This condition is associated with a number of diseases, one of the most serious being atherosclerosis. Medicaments used to lower blood cholesterol, phospholipid and triglyceride blood levels are termed hypolipidemic drugs. Presently four major lipid lowering agents are available; clofibrate, D-thyroxine, nicotinic acid and cholestyramine; [R. I. Levy and D. S. Fredrickson, Postgraduate Medicine, vol. 47, pps. 130–136 (1969)].

Prior to this invention there has been a great need for an effective antihyperlipemic agent which is low in toxicity and is relatively free of undesirable side effects. For example, it is believed that coronary artery disease and atherosclerosis in man are associated with an abnormally high concentration of cholesterol and other lipids in the blood stream. Of particular significance is the concentration of the β-lipoprotein fraction in the blood. The reduction of the amount of these lipids, including not only free and esterified cholesterol, but also phospholipids and triglycerides, is of major importance in the prevention and treatment of coronary artery disease, atherosclerosis, other vascular and heart ailments and disorders of lipid metabolism.

It is therefore an object of this invention to provide a method for reducing plasma lipid levels, particularly cholesterol, triglyceride and phospholipid levels. Another object is to provide a pharmaceutical composition capable of lowering plasma lipid levels when internally administered. Still another object is to provide such reductions without untoward side effects. A further object is to provide pharmaceutical compositions suitable for oral administration. A still further object is to provide such compositions which effectively lower the β-lipoprotein fraction of serum lipids.

SUMMARY OF THE INVENTION

There is provided by the present invention crystalline calcium α-p-chlorophenoxyisobutyrate monohydrate having the empirical formula $C_{10}H_{10}ClO_3Ca_{1/2} \cdot H_2O$.

There is further provided by the present invention the method of reducing an elevated concentration in the blood of cholesterol, triglycerides and/or low density lipoproteins (LDL) and/or increasing the fibrinolytic activity of said blood and/or decreasing platelet aggregation in said blood which comprises orally administering to a patient an effective dose of a mixture comprising one part by weight of calcium α-p-chlorophenoxyisobutyrate and about 0.5 to 4 parts by weight of calcium carbonate, preferably wherein the calcium α-p-chlorophenoxyisobutyric acid is crystalline calcium α-p-chlorophenoxyisobutyrate monohydrate having the empirical formula $C_{10}H_{10}ClO_3Ca_{1/2} \cdot H_2O$, and preferably wherein use is made of about 1 to 2 parts by weight of calcium α-p-chlorophenoxyisobutyrate and particularly wherein the daily dose of calcium α-p-chlorophenoxyisobutyrate is about one to two grams and that of calcium carbonate is about 1 to 4 grams.

There is further provided by the present invention a composition in unit dosage form effective upon oral administration for the purpose of reducing an elevated concentration in a human's blood of cholesterol, triglycerides and/or low density lipoproteins or increasing the fibrinolytic activity of said blood or decreasing platelet aggregation in said blood which comprises a mixture of one part by weight of calcium α-p-chlorophenoxyisobutyrate and about 0.5 to 4 parts by weight of calcium carbonate, preferably wherein the calcium α-p-chlorophenoxyisobutyric acid is crystalline calcium α-p-chlorophenoxyisobutyrate monohydrate having the empirical formula $C_{10}H_{10}ClO_3Ca_{1/2} \cdot H_2O$, and preferably containing about 1 to 2 parts by weight of calcium carbonate per part by weight of calcium α-p-chlorophenoxyisobutyrate, and particularly wherein the weight of calcium α-p-chlorophenoxyisobutyrate is about 250 mgm. to 500 mgm. and that of calcium carbonate is about 500 mgm.

The physiological results specified above usually take place simultaneously and are measured in the laboratory by determining concentrations in blood of cholesterol and triglycerides. These concentrations in high-fat diet hypercholesterolemic rats were found to be reduced further by the combinations of the present invention than by either of its components given along in a practical dose.

The two active ingredients of the present invention are formulated in unit dosage form as is customary in the pharmaceutical industry, that is, as capsules, tablets, powders for reconstitution, suspensions, emulsions and the like which are suitable for oral use and may contain, if desired, various pharmaceutical carriers, excipients, diluents and the like, including those specified in U.S. Pat. No. 3,262,850. In man the daily dosage, usually given in divided form, is as specified above and also may be varied by the physician depending upon the weight of the subject, the nature of the patient's condition and the intensity of the effect desired.

The following examples are given in illustration of, but not in limitation of, the present invention.

DESCRIPTION OF THE PREFERRED EMBODIMENTS

EXAMPLE 1

Calcium α-p-chlorophenoxyisobutyrate

Exactly 40 g. (0.1863 mole) of α-p-chlorophenoxyisobutyric acid [Fawcett, C. H. et al., Ann. Appl. Biol. 40, 231–243 (1953); Gilman, H. et al., J. Am. Chem. Soc. 77, 6644–6646 (1955)] was dissolved in 400 ml. of n-butanol in a 2 l round-bottom flask equipped with a reflux condenser. Water, 80 ml., and $CaCO_3$ (Fisher; 9.326 g.; 0.0932 mole) were added and the mixture was heated at reflux for 24 hours. A heavy, white crystalline precipitate formed. The mixture was cooled to about 20° C. and the solid was collected by filtration. It was washed on the filter with enough acetone to remove nearly all of the n-butanol and the product was dried in vacuo over $P_2O_5$ to produce a 95% yield of crude product which was purified by dissolution in 240 ml. of dimethylformamide at about 50° C. and filtration through analytical grade paper (S & S No. 576). Upon addition to this filtrate of an equal volume of filtered, deionized water the purified product precipitated and was collected by filtration, slurried twice with 500 ml. portions of acetone and finally collected by filtration and dried as before, yield 93% of the crystalline product. Its infrared spectrum (KBr pellet) and elemental analyses were consistent with the expected product, as the monohydrate.

Anal. calcd. for $C_{10}H_{10}ClO_3Ca_{1/2} \cdot H_2O$: C, 47.71; H, 4.81; Cl, 14.00; $H_2O$, 7.16; Ca, 7.96. Found: C, 47.83; H, 4.95; Cl, 13.67; $H_2O$, 7.36; Ca, 7.75.

EXAMPLE 2

Synthesis of Ca p-chlorophenoxyisobutyrate

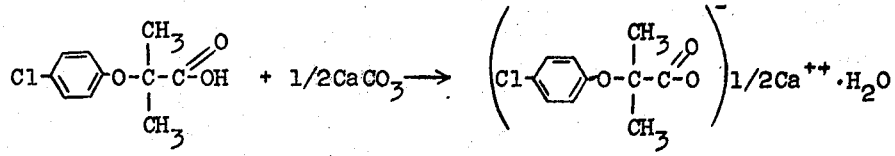

| (CPIB) 214.66 | ½(100.09)=50.045 | 233.69 + 18.02 |
|---|---|---|
| p-CPIB | | 64.4 gm. |
| Butanol | | 650 ml. |
| $CaCO_3$ | | 16 gm. |
| Water deionized | | 140 ml. |
| DMF | | 460 ml. |
| Water | | 1050 ml. |
| Acetone | | 750 ml. |

1. Dissolve the CPIB in the butanol in a 3 liter beaker.
2. Add the $CaCO_3$ to 140 ml. water and add the resulting slurry to 1 above.
3. Turn on heat to 45° while stirring for 15 min Slurry thickens up. Bubbles form. Add more butanol to allow thorough stirring.
4. Continue stirring for 1¾ hr. at 35°–40°.
5. Cool to 23°.
6. Filter through S&S 604 paper and wash with acetone.
7. Dissolve the filter cake in dimethylformamide (DMF); add more if needed to completely solubilize the CaCPIB.
8. Filter through 604 paper into 1050 ml. water and allow to stand overnight. Residue on filter is a brownish solid. The filtrate forms a white voluminous precipitate when it hits the water. Wash filter cake with DMF.
9. Filter the new precipitate through 604 paper and wash with acetone.
10. Slurry the filter cake in 800 ml. acetone for 15 min.
11. Collect by filtering through 604 paper and wash with acetone.
12. Dry overnight at 45° under vacuum.

Yield: 70 gm. = 93%.

EXAMPLE 3

Synthesis of Ca p-chlorophenoxyisobutyric acid.

Object: To prepare the title compound for development work.

Cl—⌬—O—C(CH₃)₂—C(=O)—OEt  $\xrightarrow{\text{NaOH, HCl}}$  Cl—⌬—O—C(CH₃)₂—C(=O)—OH  $\xrightarrow{\frac{1/2 \text{CaCO}_3}{50.05}}$ clofibrate – 242.71                    214.16

Cl—⌬—O—C(CH₃)₂—C(=O)—O⁻ · 1/2 Ca⁺⁺ · H₂O 251.71

| Formula: | | |
|---|---|---|
| Clofibrate | 150.0 gm. | |
| NaOH | 49.5 gm. | |
| CH₃OH | 750.0 ml. | |
| H₂O, deionized q.s. | | |
| HCl 6N q.s. | | |
| n-butanol | 1075 ml. | |
| CaCO₃ | 30.9 gm. | |
| H₂O q.s. | | |
| DMF | 2900 ml. | |
| Acetone q.s. | | |

Procedure:
1. Dissolve clofibrate in CH₃OH in a 3 liter flask.
2. Dissolve the NaOH in 150 ml. water and add to the clofibrate solution while warm (38°).
3. Warm the reaction vessel to 62° C. then slowly allow the system to drop down to R. T. (total time 3 hrs.).
4. Flash off the methanol under vacuum at 50° C. — white residue remains on the flask wall.
5. Add 350 ml. water to the residue until a solution forms.
6. Filter the solution over diatomaceous earth (Dicalite) and wash well with 2 × 75 ml. portions of water; pH = 10.1.
7. Acidify the filtrate to pH 1 with 6N HCl — white crystalline solid precipitates from solution.
7a. Collect the precipitate by filtration and wash with water until the fluid is free of Cl⁻.
8. Dissolve the wet cake in 1075 ml. butanol.
9. Add 30.9 gm. CaCO₃ slurried in 270 ml. water.
10. Heat at 50°–55° for 2 hrs.
11. Collect by filtering through No. 604 paper and wash with acetone.
12. Dissolve the Ca p-chlorophenoxyisobutyrate in 2900 ml. DMF at 50°.
13. Filter through S&S No. 604 paper into 3500 ml. of water and allow to stand for overnight.
14. Collect the white precipitate by filtration through S&S 604 paper and wash with 1 L of acetone.
15. Place the filter cake in 1 L of acetone in a beaker and break up the lumps and slurry for 10 minutes more.
16. Filter the slurry.
17. Dry the filter cake overnight at 50° under vacuum.

Yield: 133 gm. of bulky white odorless crystalline calcium p-chlorophenoxyisobutyrate monohydrate.
Solid bulk density 0.17 – 0.19 gm./ml.

EXAMPLE 4

Calcium p-chlorophenoxyisobutyrate monohydrate 260 mg. and calcium carbonate 500 mg. per capsule

| Formula: | wt/capsule | wt/100 caps. |
|---|---|---|
| CaCPIB (Calcium p-chlorophenoxy-isobutyrate monohydrate) | 260 mg. | 26.00 gm. |
| Calcium Carbonate USP | 500 mg. | 50.00 gm. |
| Colloidal Magnesium Aluminum Silicate (Veegum F) | 21 mg. | 2.10 gm. |
| Magnesium Stearate USP | 4 mg. | 0.40 gm. |
| Dioctyl sodium sulfosuccinate | 5.2 mg. | 0.52 gm. |
| TOTAL | 790 mg. | 79.02 gm. |

Procedure:
1. Dissolve the dioctyl sodium sulfosuccinate in 10 ml. of methylene chloride and wet granulate the CaCPIB; extra CH₂Cl₂ can be used if needed for the granulation.
2. Dry the wet granulation in vacuum over at 40° C.
3. Mix the other ingredients with each other and pass them through a metal screen (60 mesh).
4. Pass the dried granulation through metal screen (60 mesh) and mix it with the blend in step 3; blend the total powders on a merry-go-round.
5. The blend was slugged on a single punch machine with a ¾ inch punch. Then the slugs were passed through a metal screen 14 mesh and 30 mesh and the resulting granulation was filled into size O capsules, white body, red caps. Disintegration in artificial gastric juice (AGF) was 5–6 minutes and in H₂O was 11–12 minutes.

EXAMPLE 5

Calcium p-Chlorophenoxyisobutyrate 500 mg. and Calcium Carbonate 500 mgm. Tablets Purpose: To prepare a 100 tablet batch of the above tablets by wet granulation method.

| Formula<br>Primary Blend | Per Tab. | 100 Tabs. |
|---|---|---|
| Calcium p-chlorophenoxyisobutyrate monohydrate | 500 mg. | 50.0 gm. |
| Calcium carbonate | 500 mg. | 50.0 gm. |
| Gelatin | 30 mg. | 3.0 gm. |
|  | 1.030 gm. | 103.0 gm. |
| Final Granulation | Per Tab. | 95 Tabs. |
| Primary Granulation | 1.03 gm. | 97.85 gm. |
| Microcrystalline Cellulose | 0.21 gm. | 19.95 gm. |
| Magnesium Stearate | 0.01 gm. | 0.95 gm. |
| Cholestyramine Resin, Mead Johnson | 0.02 gm. | 1.90 gm. |
|  | 1.27 gm. | 120.65 gm. |

Primary Granulation yield ≅ 98.0 gm.

Procedure:

Primary

1. Pass the calcium CPIB and the calcium carbonate through a 30 mesh metal screen to break up agglomerates.
2. Blend the powders thoroughly.
3. Prepare a 5% solution of the gelatin by suspending in cold water and heating to 55° C.
4. Wet the powders in mortar using the gelatin solution, until desired consistency is reached. An additional 30 cc. of water was added to the granulation to achieve the desired wetness.
5. Dry in vacuum oven for 16–18 hours at 25 inches of vacuum, 40° C.

Final

Pass the dry granules through a 14 mesh metal screen. Pass the magnesium stearate through a 100 mesh nylon screen, blend all ingredients in final blend thoroughly.

Compress on 0.81 inch × 0.362 inch. Capsule shaped, double bisected punch using Stokes single punch machine.

Results

Weight — 1.27 gm., 1.25 gm., 1.27 gm. — Avg. = 1.26 gm.
Hardness — 21 – 23 kg.
Thickness — 6.65 to 6.70 mm.
Friability — 0.1%

EXAMPLE 6

CaCPIB (250 mg.) and (250 mg.) CaCO₃ granulation for oral suspension (per 5 ml.)

Object: To prepare a small batch of CaCPIB and CaCO₃ (500 mg. of each per teaspoon) as a dry powder to be reconstituted.

| Formula | wt/25cc. or 5 doses | wt/250cc or 50 doses |
|---|---|---|
| Calcium p-chlorophenoxy-isobutyrate monohydrate | 2.5 gm. | 25.0 gm. |
| Calcium Carbonate USP | 2.5 gm. | 25.0 gm. |
| Starch USP | 0.50 gm. | 5.00 gm. |
| Sodium carboxymethyl-cellulose | .45 gm. | 4.50 gm. |
| Sucrose USP | 10.00 gm. | 100.00 gm. |
| Flavors | 225 mg. | 2.25 gm. |
| Yellow No. 5 1% dry trituration | .150 gm. | 1.50 gm. |
|  | 163.25 | 163.25 |

Procedure:

1. CaCPIB and CaCO₃ were mixed, then wet granulated with a mixture of starch slurry in 45 ml. H₂O, the wet granulation was passed through metal screen 14 mesh and was left in vacuum oven to dry.
2. The dry granulation was screened through a 20 mesh, then a 60 mesh screen. The other ingredients were added to it, mixed well and blended for 30 min. The blend was then passed through metal screen No. 60 to break up lumps. 16.325 gm. should be mixed with enough water to make 25 ml. suspension resulting in 500 mg. of CaCPIB and CaCO₃ per 5 ml. But this was not possible. Water to make 25 ml. suspension was only 10 ml. which did not wet all the powder to make a free flowing suspension, water was increased to make a 50 ml. suspension at 250mg./5 ml.

EXAMPLE 7

CaCPIB (500 mg.) plus CaCO₃ (500 mg.) per teaspoon (5 ml.) as oral suspension

| Formula | wt/5 doses | wt/100 doses |
|---|---|---|
| Calcium CPIB (calcium p-chlorophenoxyisobutyrate monohydrate) (200 mesh) | 2.500 | 50.00 gm. |
| Calcium carbonate USP | 2.500 | 50.00 gm. |
| Starch USP | 0.500 | 10.00 |
| Flavors | 0.175 | 3.50 |
| Ammonium Glycyrrhizinate ("Glycamil"; Marcel Quarre & Co., Paris, France) | 0.075 | 1.50 |
| Sodium carboxymethyl-cellulose (NaCMC) | 0.450 | 9.00 |
| Sodium benzoate | 0.025 | 0.50 |
| Atmos-300 liquid food emulsifier sprayed on sucrose | 1.000 | 20.00 |
| Yellow No. 5, 1% Dry trituration | 0.150 | 3.00 |
| Sucrose USP | 10.000 | 200.00 |
| H₂O q.s. | 25.000 | 500.00 |

Procedure:

1. Mix the starch with 35 ml. of water and wet granulate the CaCPIB in a mortar with a pestle; more water can be added until a uniform wet granulation is reached.
2. Dry the wet granulation in vacuum oven at 42° C. for 16 hours.
3. Pass the dry granulation through 14, 30 and 60 mesh metal screens.
4. Dissolve the NaCMC in 100 ml. of water, use more water until you get complete solution, add this solution to the powder in step number 3 in a mortar and mix well until uniform paste is formed.
5. Weigh the Glycamil, all the flavors and sodium benzoate, mix them well and add into the paste in step number 4, mix well, 25-30 ml. H₂O could be added if needed to wet and mix all powders.
6. Dissolve the dye in 35-40 ml. H₂O and mix with the paste.

7. Dissolve the Atmos in 50 ml. H₂O and add to the paste, and as you mix them a uniform suspension is formed.

8. At this point the CaCO₃ was added and mixed well, then the sucrose was added mixed well until a uniform suspension was resulted.

9. Add water to make up to volume then mix well.

10. Pass the resulting suspension through a 100 nylon mesh.

11. The suspension was filled in 1 oz. flint bottles 25 ml. per bottle.

EXAMPLE 8

Calcium p-chlorophenoxyisobutyrate monohydrate 260 mg. and calcium carbonate 250 mg. per capsule

| Formula | wt/capsule | wt/100 capsules |
|---|---|---|
| Calcium p-chlorophenoxy-isobutyrate monohydrate (CaCPIB) | 260 mg. | 26.000 g. |
| Calcium Carbonate USP | 250 mg. | 25.000 g. |
| Colloidal Magnesium Aluminum Silicate "Veegum F" | 21 mg. | 2.100 g. |
| Dioctyl sodium sulfo-succinate | 4 mg. | 0.400 g. |
| Magnesium stearate USP | 5 mg. | 0.500 g. |
| TOTAL | 540 mg. | 54.000 g. |

Procedure:

1. Dissolve the dioctyl sodium sulfosuccinate in 20 ml. methylene chloride by stirring.

2. Wet granulate the calcium p-chlorophenoxyisobutyrate monohydrate with the solution on step number 1.

3. Let the wet granulation dry in the hood then in vacuum oven at 40° C.

4. Pass the dried granulation through metal screens 20 and 40 mesh.

5. Weigh the other ingredients and mix them with the dry screened granulation, then blend the mixture on merry-go-round for 30 minutes.

6. The blend was then pressed into slugs.

7. The slugs were passed through metal screens 20 and 30 mesh, the resulting granulation was slugged again to get a denser granulation. Passed through No. 10, 20 and 30 mesh screens.

8. The granulation was filled into size no. 1 capsules.

9. Disintegration time in AGF was 5 minutes and in water 7 minutes.

We claim:

1. The method of reducing an elevated concentration in the blood of cholesterol, triglycerides or low density lipoproteins which comprises orally administering to a hyperlipidemic patient an effective lipid-lowering dose of a mixture comprising one part by weight of calcium α-p-chlorophenoxyisobutyrate and about 0.5 to 4 parts by weight of calcium carbonate.

2. The method of claim 1 wherein the calcium α-p-chlorophenoxyisobutyrate is crystalline calcium α-p-chlorophenoxyisobutyrate monohydrate having the empirical formula $C_{10}H_{10}ClO_3Ca_{1/2} \cdot H_2O$.

3. The method of claim 1 wherein use is made of about 1 to 2 parts by weight of calcium carbonate per part by weight of calcium α-p-chlorophenoxyisobutyrate.

4. The method of claim 3 wherein the daily dose of calcium p-chlorophenoxyisobutyrate is about 1 to 2 grams and that of calcium carbonate is about 1 to 4 grams.

5. The method of claim 4 wherein the calcium α-p-chlorophenoxyisobutyrate is crystalline calcium α-p-chlorophenoxyisobutyrate monohydrate having the empirical formula $C_{10}H_{10}ClO_3Ca_{1/2} \cdot H_2O$.

6. A composition in unit dosage form effective upon oral administration for the purpose of reducing an elevated concentration in a hyperlipidemic human's blood of cholesterol, triglycerides or low density lipoproteins which comprises an effective lipid-lowering amount of a mixture of one part by weight of calcium α-p-chlorophenoxyisobutyrate and about 0.5 to 4 parts by weight of calcium carbonate.

7. A composition of claim 6 wherein the calcium α-p-chlorophenoxyisobutyrate is crystalline calcium α-p-chlorophenoxyisobutyrate monohydrate having the empirical formula $C_{10}H_{10}ClO_3Ca_{1/2} \cdot H_2O$.

8. A composition of claim 6 containing about 1 to 2 parts by weight of calcium carbonate per part by weight of calcium α-p-chlorophenoxyisobutyrate.

9. A composition of claim 6 wherein the weight of calcium p-chlorophenoxyisobutyrate is about 250 mgm. to 500 mgm. and that of calcium carbonate is about 500 mgm.

10. A composition of claim 9 wherein the calcium α-p-chlorophenoxyisobutyrate is crystalline calcium α-p-chlorophenoxyisobutyrate monohydrate having the empirical formula $C_{10}H_{10}ClO_3Ca_{1/2} \cdot H_2O$.

* * * * *